US005707653A

United States Patent [19]
Goldberg

[11] Patent Number: 5,707,653
[45] Date of Patent: Jan. 13, 1998

[54] ULCER TREATING COMPOSITION COMPRISING SUFALCRATE AND ANTIBIOTIC

[76] Inventor: Arthur H. Goldberg, 624 Sand Hill Cir., Menlo Park, Calif. 94025

[21] Appl. No.: 544,444

[22] Filed: Nov. 17, 1995

[51] Int. Cl.⁶ .................................................. A61K 31/70
[52] U.S. Cl. .................... 424/464; 424/493; 424/499; 514/24; 514/53
[58] Field of Search .............. 514/53, 24; 424/464, 424/493, 499

[56] References Cited

U.S. PATENT DOCUMENTS 5,538,954  7/1996  Koch et al. ............................. 514/53

FOREIGN PATENT DOCUMENTS 0 403 048  12/1990  European Pat. Off. ........ A61K 31/70

OTHER PUBLICATIONS

Yokel et al, "Selective Adherence of A Sucralfate-Tetracycline Complex to Gastric Ulcers: Implications for the Treatment of Helicobacter Pylori", Biopharmaceutics and Drug Disposition, vol. 16, pp. 475-479, 1995.

Derwent Abstracts 90-377786, "Basic Aluminum Sucrose Sulphate Compositions", Dec. 1990.

*Primary Examiner*—Frederick Krass

[57] ABSTRACT

Pharmaceutical compositions comprising an antibiotic adsorbed onto a disaccharide polysulfate-aluminum compound such as sucralfate are effective for the treatment of ulcers. The composition adherently coats the ulcer, protecting it while imparting an antibiotic activity which accelerates healing.

19 Claims, No Drawings

ULCER TREATING COMPOSITION COMPRISING SUFALCRATE AND ANTIBIOTIC

INTRODUCTION TO THE INVENTION

This invention relates to a method and medication for the treatment of an ulcer. A composition comprising an antibiotic adsorbed onto a disaccharide polysulfate-aluminum compound is contacted with the ulcer site. The composition adherently coats the ulcer, protecting it while imparting an antibiotic activity which accelerates healing.

In a preferred embodiment, this method is utilized for treatment of an internal ulcer. After ingestion, the disaccharide polysulfate-aluminum compound with adsorbed antibiotic preferentially binds to the ulcer. Thus concentrated, its protective and healing properties are enhanced.

BACKGROUND OF THE INVENTION

Numerous attempts have been made to solve the problem of treating ulcers. No entirely satisfactory solution is available. There is a real need for a safe and effective product which will provide for their relief and cure.

Disaccharide polysulfate-aluminum compounds are accepted medications for the treatment for peptic ulcers. Such compounds are disclosed in U.S. Pat. No. 3,432,489 to Nitta et al (Nitta), which is incorporated herein by reference. Typical compounds are sucrose polysulfate-aluminum compounds, lactose polysulfate-aluminum compounds and maltose polysulfate-aluminum compounds. The sulfur and aluminum contents are commonly from 7–13% and 11–24%, respectively and, therefore, generally contain from 1–4 aluminum atoms per sulfur atom.

Nitta discloses the internal use of these compounds in the treatment of peptic ulcers by oral administration. Such ulcers have a pathology characterized by erosion of the mucosa of the alimentary canal. The major areas where mucosa occurs include the mouth, the esophagus, the stomach (gastric mucosa) and the duodenum (duodenal mucosa). The mucosa is located anatomically in areas bathed by acid and which normally have a pH ranging from about 1.0 to 4.0.

One of the compounds disclosed in Nitta is a sucrose polysulfate aluminum compound referred to in The Merck Index, Merck & Co., Inc., Rahway, N.J., 10th Edition, 1983 at number 8755 as sucralfate. This compound is currently marketed as an anti-ulcerative agent. Disaccharide polysulfate-aluminum complexes are frequently referred to herein for the purposes of simplicity as sucralfate.

Sucralfate is now also recognized by those skilled in the art as being useful in the treatment of peptic ulcer disease (Borrers et al, Am. J. Surg., 148 (1984) pp 809–12) and in short term duodenal and gastric ulcer healing (Halter, S. Afr. Med. Journal 23 (1984) 996–1000). In addition, oral ulcers or mucositis which have developed as a direct consequence of treatment of patients receiving chemotherapy or radiation or both have been treated with sucralfate suspension. (Solomon, Cell 351, 459 (August, 1986).

Disaccharide polysulfate-aluminum compounds such as sucralfate have also previously been developed and are known for the purpose of protecting other kinds of ulcers. In, for example, U.S. Pat. No. 4,945,084, there is described a method for treating hemorrhoids. There a composition comprising a thick paste of disaccharide polysulfate-aluminum compound on a pharmaceutical carrier is described. The composition may further contain any number of pharmacological agents including anesthetics, vaso-constructors, protectants, counterirritants, astringents, wound healing agents, antiseptics, keratolytics and anticholinergics. These agents may also include antibiotics.

In addition to the treatment of internal ulcers of the alimentary canal as described above, these compounds may be applied to topical or external ulcers. This includes scrapes or other injuries of the skin. Indeed, they may be employed to treat virtually any such tissue wound, wherever situated on the body.

These treatments, however, do not adequately address one of the problems of ulcers. They are commonly a site of infection. Disaccharide polysulfate-aluminum compounds do not combat infection. Moreover, the coatings they develop over a wound tissue may actually interfere with the treatment of the infection and thereby retard the healing process.

It is, therefore, an object of the present invention to provide an improved composition for use in the treatment of ulcers.

It is a further object of the instant invention to provide a method for treating ulcers to control or relieve their symptoms at a wound site.

It is a still further object of the instant invention to provide an improved means for treatment of internal ulcers.

Another object of the instant invention to provide a preparation which forms a protective barrier over an ulcer and also acts as a carrier which enhances antibiotic activity at the wound site.

This invention provides a method for treating ulcers through contact with a composition which is safe, effective and comprises an antibiotic adsorbed onto a disaccharide polysulfate-aluminum compound.

DESCRIPTION OF THE INVENTION

This invention provides a composition and a method for treating ulcers. These ulcers may be situated anywhere on or within the body.

The composition of the instant invention comprises an antibiotic adsorbed (or complexed) onto a disaccharide polysulfate-aluminum compound such as sucralfate. This composition may be used in the same manner as sucralfate alone. It may be applied to an external ulcer in powdered form or, more typically, in a pharmaceutically acceptable dispersant. With internal ulcers, these compositions are normally ingested so as to reach the involved area. They may simply be taken orally or injected into the area of the body where the ulcer is located.

Treatment of ulcer wounds is often complicated by infection. Infection presents a particular problem when the ulcer being treated is internal to the body. A localized application is difficult to achieve. Large doses of antibiotic must normally be ingested to obtain an effective therapeutic concentration over sufficient time to combat such an infection within the body.

This problem is only compounded where sucralfate or other disaccharide polysulfate-aluminum compounds are employed to treat an ulcer. The protective covering formed by sucralfate may shield the infection. This makes it difficult for an effective amount of the antibiotic to reach it. Consequently, healing may be greatly retarded.

In accordance with the present invention, however, this drawback is avoided. With the present compositions, antibiotic is adsorbed onto the disaccharide polysulfate-aluminum compounds prior to application. As a consequence, antibiotic is carried directly and preferentially to the ulcer site by these compounds. The antibiotic is also retained there when the disaccharide polysulfate-aluminum compound adheres to the wound. This increases its effective concentration in the region of infection. Consequently, healing is accelerated, rather than retarded.

An important aspect of this invention is the selection of an appropriate antibiotic. The antibiotic must be one which adsorbs onto (or complexes with) the disaccharide polysulfate-aluminum compound. This interaction ensures that the antibiotic is selectively carried to the ulcer site, and is held there by the compound. This increases its effective concentration and pharmacological effect.

Most antibiotics have no affinity towards a disaccharide polysulfate-aluminum compound. They do no more than mix with a sucralfate. Consequently, in an aqueous environment such as that in the alimentary canal of the body, they are rapidly diluted. They are also eluded from the sucralfate and/or wound site, and their effectiveness is rapidly lost.

It has been discovered, however, that select antibiotics adsorb onto sucralfate. The resultant combination or complex is stable and permits targeting of the location of antibiotic. Representative adsorbable antibiotics include nalidixic acid, doxycycline hyclate and tetracycline. Others may readily be determined.

The absorbability or affinity of an antibiotic to complex with a disaccharide polysulfate-aluminum compound may be determined by dissolving an antibiotic in an aqueous slurry of sucralfate. The concentration of dissolved antibiotic can be monitored by spectroscopic analysis or other technique. If adsorbable, the concentration of dissolved antibiotic will drop, only to stabilize when the sucralfate-antibiotic complex reaches equilibrium or saturation.

Antibiotics having an affinity toward sucralfate are desirably incorporated into the present compositions in from 0.2% to 5% by weight of compound. These antibiotics may be concentrated on an ulcer through their linkage to sucralfate and its property of preferentially binding to a wound site. This ensures that a therapeutically effective amount of antibiotic is present to combat infection and to facilitate healing of the ulcer.

Once the complex of antibiotic and disaccharide polysulfate-aluminum compound has been formed as described above, it can be separated from the aqueous dispersant and dried. It remains stable in this form and can be administered directly as a powder or mixed with a pharmaceutically acceptable dispersant to permit formation of a tablet or another slurry. The composition is normally administered from 1 to 4 times over the course of a single day. The administration is continued for as many days as are necessary to relieve the condition being treated.

The dosage amount of sucralfate composition administered in accordance with the invention need not be great. Sucralfate has been found to bind preferentially to a wound site as opposed to normal tissue. As a result, the present compositions concentrate on and adhere to an ulcer. This significantly reduces the amount(s) of disaccharide polysulfate-aluminum compound and/or antibiotic which would otherwise be needed for optimum therapeutic effect.

For an external or topical application, a very light coating may be applied directly to the ulcer site. As little as 10 milligrams per square centimeter, more desirably at least 25 mg/cm$^2$ of particulate composition may be applied. This may be performed by dusting the ulcer with a free-flowing, powder form of the present composition.

The composition may also be diluted with a pharmaceutically acceptable dispersant and then applied directly to the ulcer. The dispersant may be any conventional material for topical application. It may conveniently be an ointment composed, for example, of petroleum jelly or lanolin or other suitable carriers. Other representative dispersants which may be used are disclosed in U.S. Pat. No. 4,626,433 of Gros, the disclosure of which is incorporated herein by reference.

For internal ulcers which cannot be treated directly, the composition may be ingested in any dispersed form. Thus, the composition may be compacted into a tablet with a solid such as lactose or starch or other conventional binder. Similarly, it may be mixed with an organic liquid such as alcohol or glycol and then encapsulated. An aqueous slurry may also be employed. Such a slurry normally comprises at least 70% liquid by total weight. The normal dosage for internal application will range from 2 to 8 grams of composition in a twenty-four hour period.

Any of these forms of the present composition may be used to treat internal ulcers. After ingestion, the tablets readily disintegrate forming an aqueous slurry within the alimentary canal. This or one of the other slurries of the present invention constitutes a preferred means of transmitting the composition to an ulcer site. For ulcers of the large intestine, bladder and/or certain other regions, rather than causing the composition to pass through most of the alimentary canal, it may be desirable to inject the composition directly into the area where the ulcer is located.

Normally, the composition is maintained at the ulcer site for a sufficient time to ensure that a desirable amount of the composition will bind to the ulcer. In most cases, this occurs inherently during administration because as little as 15 seconds, more desirably 30 seconds, is usually enough. Only in rare cases is any special effort necessary. Thus, for example, where an oral ulcer is being treated, the slurry should be held temporarily in the mouth and then may be expectorated or swallowed.

The following examples are not intended to limit the present invention, but are merely illustrative thereof. It is understood that one of ordinary skill in the art would be able to make substitutions, change proportions, or make other variations, all within the scope of the teachings and without departing from the spirit of the invention and without undue experimentation.

EXAMPLE 1

The affinity of various antibiotics toward disaccharide polysulfate-aluminum compound was tested employing a series of nine compounds.

Each antibiotic was placed in water and stirred at a temperature of 37° C. until equilibrium was reached. An aliquot was then removed and the concentration of dissolved antibiotic was determined by UV spectroscopic analysis.

Sucralfate was then added to the remaining solution. The resultant slurry was stirred for at least thirty minutes until equilibrium was again obtained. The slurry was filtered to remove its solids and a second aliquot of solution was removed. Its concentration of antibiotic was determined by the same technique used previously.

A comparison of the results of these paired analyses for representative antibiotics showed:

| Antibiotic | Change from initial analysis |
| --- | --- |
| Cephaloridine | None |
| Nalidixic Acid | Decrease |
| Doxycycline Hyclate | Decrease |
| Benzylpenicillin | None |
| Erythromycin | None |
| Sulfamethizole | None |
| Nitrofurantoin | None |
| Gentamycis Sulfate | None |
| Tetracycline | Decrease |

A decrease in the concentration of antibiotic reflects adsorption of soluble antibiotic onto particulate sucralfate. Thus, these results reveal that only three of these sample antibiotics, nalidixic acid, doxycycline hyclate and tetracycline possess the affinity required for the present invention.

EXAMPLE 2

The effectiveness of the present antibiotic-sucralfate complexes was measured in the treatment of gastric ulcers artificially induced in rabbits.

Six antral stomach wall injuries were produced by pinch biopsy in each of ten anesthetized rabbits weighing about 2.5 kg. This was performed by laparotomy. The rabbits then received 800 cGy irradiation and appropriate post-operative care.

Six days later the rabbits were food deprived for twenty-four (24) hours before administering an aqueous slurry of tetracycline-sucralfate complex by feeding tube. The rabbits were then sacrificed and their stomachs rinsed with cold saline. Biopsies of each of the six ulcer sites as well as adjacent, non-ulcerated sites were obtained. These were then quantitatively analyzed for aluminum content by electrothermal atomic adsorption spectroscopy.

A comparison of the median aluminum content for ulcer biopsies to the median content of non-ulcerated (control) biopsies was performed. The average ratio for the rabbit biopsies was 2.5. Thus the complexed antibiotic did not negate the preference of sucralfate to bind preferentially to a wound site. Its adherence there was approximately 150% greater than for non-ulcerated tissue.

EXAMPLE 3

The antimicrobial activity of a doxycycline hyclate-sucralfate complex having a weight ratio of 1:70 was determined using a modified U.S.P. turbidimetric method.

A control sample of a dilute culture of staphylococcus aureus in U.S.P. medium 3 was analyzed at 530 nm for percent transmission.. This control and samples additionally containing varying concentrations of the antibiotic alone, sucralfate alone and the complex were incubated in a 37° C. water bath. After four (4) hours, the samples were removed and their transmissions were measured as previously described. The results were as follows:

| | Percent Transmissions | |
| --- | --- | --- |
| | Initial | Final |
| Control | 100% | 56% |
| Sucralfate | — | 51.6% at 70 ug/mL |
| | | 55.5% at 35 ug/mL |
| | | 53.9% at 7 ug/mL |

| | Percent Transmissions | |
| --- | --- | --- |
| | Initial | Final |
| Doxycycline Hyclate | — | 99.2% at 1.25 ug/mL |
| | | 92.2% at 0.125 ug/mL |
| | | 91.3% at 0.1 ug/mL |
| | | 86.4% at 0.08 ug\mL |
| Complex | — | 97.5% at 70 ug\mL |
| | | 84.4% at 35 ug\mL |
| | | 69.1% at 7 ug\mL |

This data reflects that sucralfate alone exhibits no anti-microbial activity. On the other hand, complexed antibiotic has only a slightly lessened activity as compared to the uncomplexed, antibiotic control. Therefore, this example shows that a targeted medication of desired therapeutic activity is readily obtained.

EXAMPLE 4

The procedure of Example 3 is repeated substituting tetracycline and a tetracycline-sucralfate complex having a weight ratio of 1:160. The results were as follows:

| | Percent Transmissions | |
| --- | --- | --- |
| | Initial | Final |
| Control | 100% | 57.5% |
| Sucralfate | — | 59.9% at 160 ug/mL |
| | | 57.9% at 80 ug/mL |
| | | 57.5% at 16 ug/mL |
| Tetracycline | — | 101.2% at 2.4 ug/mL |
| | | 95.6% at 0.3 ug/mL |
| | | 92.7% at 0.24 ug/mL |
| | | 85.9% at 0.192 ug/mL |
| Complex | — | 94.1% at 160 ug/mL |
| | | 83.3% at 80 ug/mL |
| | | 63.2% at 16 ug/mL |

Again the antibiotic-sucralfate complex exhibits a significant anti-microbial activity, only slightly lessened from that of the antibiotic control.

The foregoing Examples are illustrative of the present invention. The scope of this invention is indicated by the appended claims, and all changes which come within the meaning and range of equivalency of these claims are intended to be embraced therein.

What is claimed is:

1. A pharmaceutical composition comprising a disaccharide polysulfate-aluminum compound and a water-soluble antibiotic, said antibiotic being adsorbed onto said compound.

2. The composition of claim 1, wherein the disaccharide polysulfate-aluminum compound is selected from the group consisting of sucrose polysulfate-aluminum compounds, lactose polysulfate-aluminum compounds and maltose polysulfate-aluminum compounds, the sulfur and aluminum contents of which are 7-13% and 11-25%, respectively.

3. The composition of claim 1, wherein the disaccharide polysulfate-aluminum compound is sucralfate.

4. The composition of claim 3, wherein the antibiotic is nalidixic acid, doxycycline hyclate or tetracycline.

5. The composition of claim 1, wherein the composition is admixed with a pharmaceutically acceptable dispersant.

6. The composition of claim 5, wherein the composition is a slurry comprising at least 70% liquid dispersant by weight.

7. The composition of claim 5, wherein the antibiotic comprises from 0.2% to 5% of the weight of the disaccharide polysulfate-aluminum compound.

8. The composition of claim 7, wherein the disaccharide polysulfate-aluminum compound is sucralfate.

9. The composition of claim 5, wherein the composition is compacted with a solid dispersant to form a tablet.

10. A method for the treatment of an internal ulcer comprising ingesting a pharmaceutically effective amount of the composition of claim 5.

11. The method of claim 10, wherein the composition is ingested orally.

12. The method of claim 11, wherein the composition comprises an aqueous slurry.

13. The method of claim 12, wherein the aqueous slurry is held in the mouth for at least 15 seconds to permit said composition to bind to an ulcer in said mouth.

14. The method of claim 10, wherein the disaccharide polysulfate-aluminum compound is sucralfate.

15. A method for the treatment of a topical ulcer comprising applying the composition of claim 1 directly to the ulcer.

16. The method of claim 15, wherein the composition is admixed with a pharmaceutically acceptable ointment.

17. The method of claim 15, wherein the disaccharide polysulfate-aluminum compound is sucralfate.

18. A pharmaceutical composition comprising the adsorption product formed by complexing a water solubilized antibiotic onto particles of a disaccharide polysulfate-aluminum compound.

19. A method for the treatment of an ulcer comprising coating the ulcer with the composition of claim 18.

* * * * *